United States Patent
Schauer et al.

(10) Patent No.: US 9,554,931 B2
(45) Date of Patent: Jan. 31, 2017

(54) PREFORMED GASTRIC BAND AND METHOD OF USE

(75) Inventors: Philip Schauer, Hunting Valley, OH (US); Stacy Brethauer, Westlake, OH (US); Bipan Chand, Oak Park, IL (US); Joseph Talarico, Naples, FL (US); Fady Moustarah, Quebec (CA)

(73) Assignee: The Cleveland Clinic Foundation, Cleveland, OH (US)

( * ) Notice: Subject to any disclaimer, the term of this patent is extended or adjusted under 35 U.S.C. 154(b) by 6 days.

(21) Appl. No.: 13/882,274

(22) PCT Filed: Nov. 1, 2011

(86) PCT No.: PCT/US2011/058787
§ 371 (c)(1),
(2), (4) Date: Aug. 21, 2013

(87) PCT Pub. No.: WO2012/061386
PCT Pub. Date: May 10, 2012

(65) Prior Publication Data
US 2013/0331642 A1    Dec. 12, 2013

Related U.S. Application Data

(60) Provisional application No. 61/408,743, filed on Nov. 1, 2010.

(51) Int. Cl.
*A61F 5/00* (2006.01)
(52) U.S. Cl.
CPC ............. *A61F 5/0063* (2013.01); *A61F 5/003* (2013.01); *A61F 5/0076* (2013.01)

(58) Field of Classification Search
CPC .... A61F 2/0004; A61F 2/0036; A61F 2/0063; A61F 5/005; A61F 5/0053; A61F 5/0063
USPC ....... 600/29–31, 37; 606/151, 153, 154, 157
See application file for complete search history.

(56) References Cited

U.S. PATENT DOCUMENTS

| | | | |
|---|---|---|---|
| 2005/0119674 A1* | 6/2005 | Gingras | 606/151 |
| 2005/0125014 A1* | 6/2005 | Duluco et al. | 606/151 |
| 2005/0234291 A1* | 10/2005 | Gingras | 600/30 |
| 2006/0142790 A1* | 6/2006 | Gertner | 606/153 |
| 2009/0157107 A1* | 6/2009 | Kierath et al. | 606/157 |

* cited by examiner

*Primary Examiner* — Charles A Marmor, II
*Assistant Examiner* — Carrie Dorna
(74) *Attorney, Agent, or Firm* — Tarolli, Sundheim, Covell & Tummino LLP

(57) ABSTRACT

One aspect of the present invention includes a preformed gastric band comprising a flexible substrate and a plurality of band members. The flexible substrate comprises oppositely disposed first and second major surfaces defined by first and second minor side portions and first and second major side portions. The first major surface includes a lower collar section and an upper band section. The plurality of flexible band members is securely connected to the upper band section and extends between the first and second minor side portions of the substrate. Each of the band members includes first and second ends that comprise an attachment mechanism for connecting the first and second ends. Each of the band members is separated from one another by a spacing region.

16 Claims, 9 Drawing Sheets

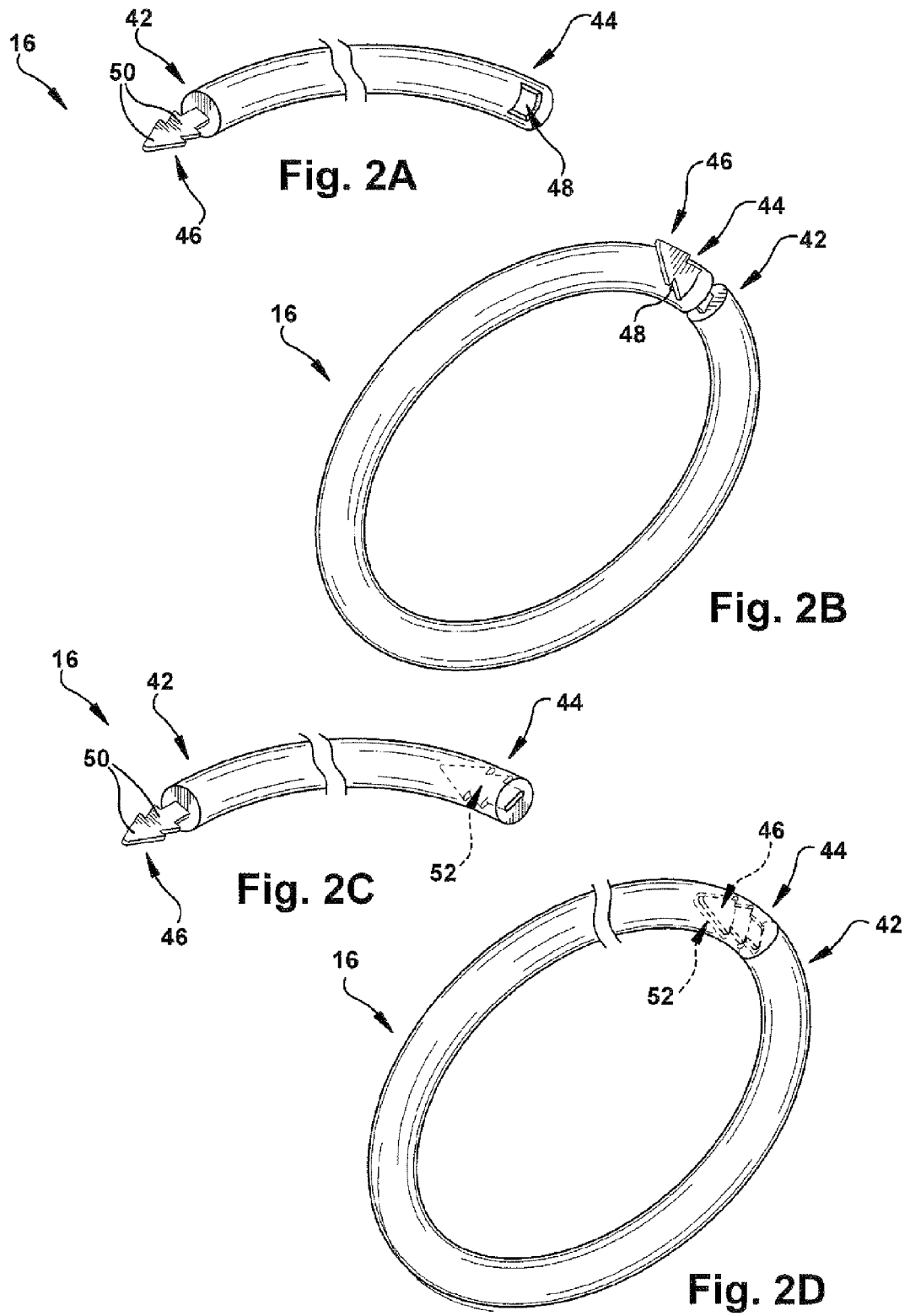

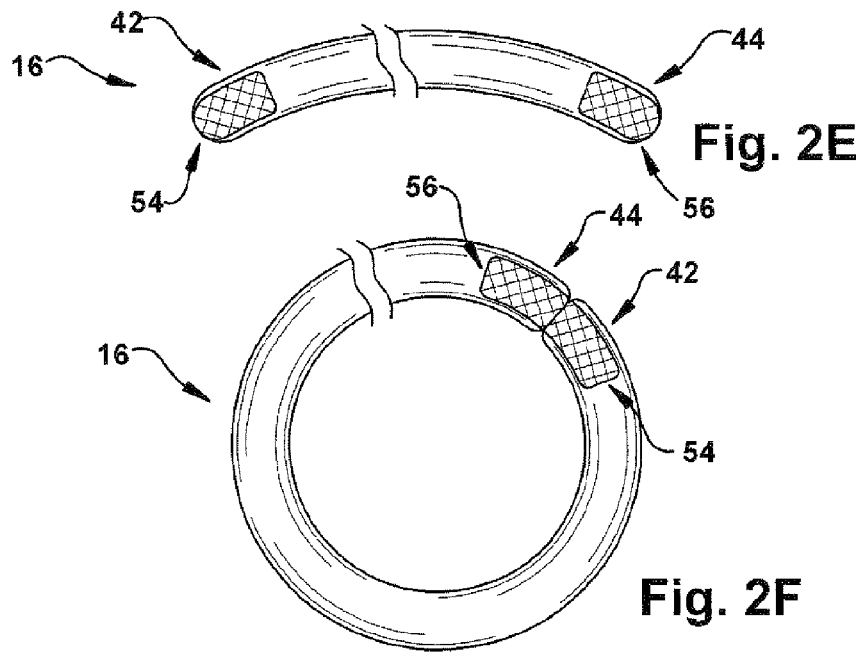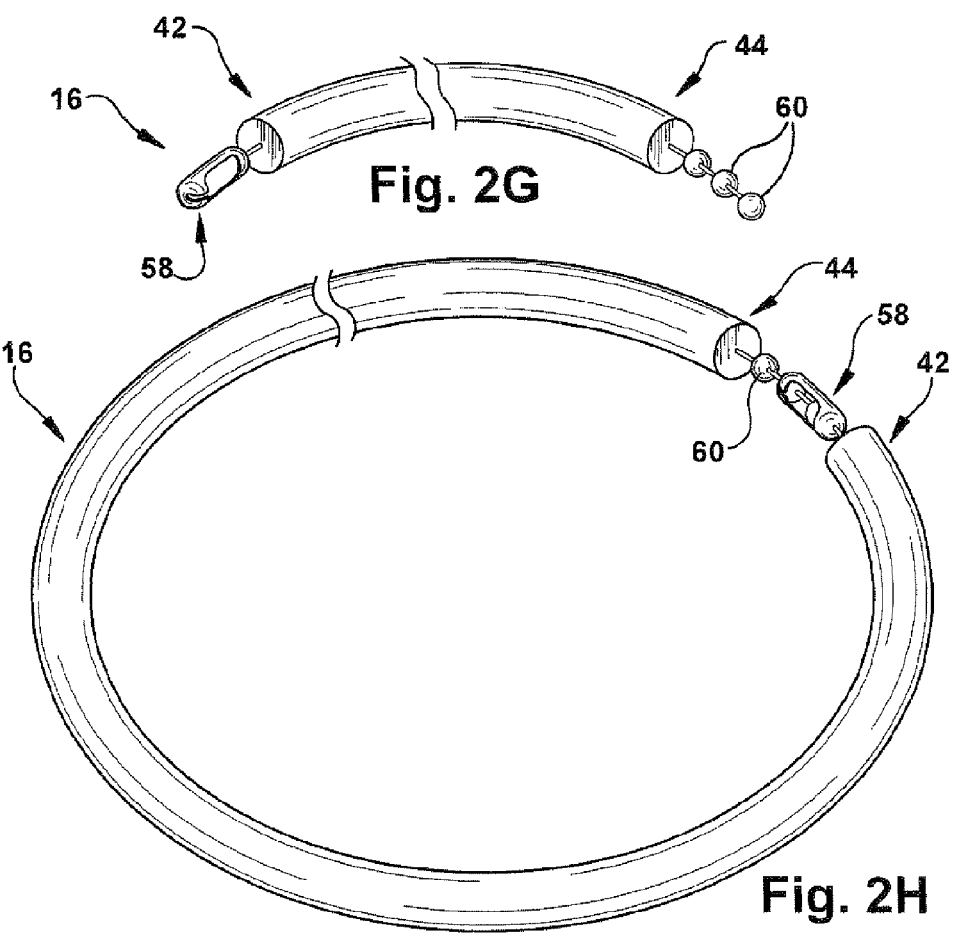

PREFORMED GASTRIC BAND AND METHOD OF USE

CROSS-REFERENCE TO RELATED APPLICATION

This application is a National Phase filing of PCT/US2011/058787, filed Nov. 1, 2011, which claims priority from U.S. Provisional Patent Application Ser. No. 61/408,743, filed Nov. 1, 2010, the subject matter of which is incorporated herein by reference.

TECHNICAL FIELD

The present invention relates generally to a preformed gastric band, and more particularly to a preformed gastric band for preventing or mitigating dilation of a gastric pouch following a gastric bypass procedure.

BACKGROUND OF THE INVENTION

Morbid obesity is a serious medical condition. Complications associated with morbid obesity include hypertension, diabetes, coronary artery disease, stroke, congestive heart failure, multiple orthopedic problems, and pulmonary insufficiency with markedly decreased life expectancy. With this in mind, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass. This procedure is highly complex and is commonly utilized to treat people exhibiting morbid obesity. Other forms of bariatric surgery include Fobi pouch, biliopancreatic diversion, and gastroplastic or "stomach stapling". In addition, implantable devices are known that limit the passage of food through the stomach and affect satiety.

Despite the many advantages associated with these procedures, drawbacks still remain. For example, it has been found that the gastric pouch created by such procedures can dilate over time and thereby lead to weight regain. In such patients, a "banded bypass" operation is performed in which surgeons create and then apply a silastic band about the gastric pouch in an effort to prevent or mitigate pouch dilation. This process is cumbersome, however, as surgeons must create the bands in the operating room, which can take up to 30 minutes or more. Additionally, such bands, once implanted, require additional invasive surgery in the event of failure.

SUMMARY OF THE INVENTION

The present invention relates generally to a preformed gastric band, and more particularly to a preformed gastric band for preventing or mitigating dilation of a gastric pouch following a gastric bypass procedure. One aspect of the present invention includes a preformed gastric band comprising a flexible substrate and a plurality of band members. The flexible substrate comprises oppositely disposed first and second major surfaces defined by first and second minor side portions and first and second major side portions. The first major surface includes a lower collar section and an upper band section. The plurality of flexible band members is securely connected to the upper band section and extends between the first and second minor side portions of the substrate. Each of the band members includes first and second ends that comprise an attachment mechanism for connecting the first and second ends. Each of the band members is separated from one another by a spacing region.

In another aspect of the present invention, a method is provided for restricting expansion of a gastric pouch in a subject. The gastric pouch is formed by a bariatric procedure and includes an anastomosis. One step of the method includes providing a gastric band comprising a flexible substrate and a plurality of band members disposed thereon. The flexible substrate comprises oppositely disposed first and second major surfaces defined by first and second minor side portions and first and second major side portions. The first major surface includes a lower collar section and an upper band section. The plurality of flexible band members is securely disposed on the upper band section and extends between the first and second minor side portions of the substrate. Each of the band members includes first and second ends that comprise an attachment mechanism for connecting the first and second ends. Each of the band members is separated from one another by a spacing region. After determining the dimensions of the gastric pouch, the gastric band is optionally sized based on the determined dimensions of the gastric pouch. The gastric band is then secured to the gastric pouch. The gastric band prevents or mitigates dilation of the gastric pouch.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2A is a perspective view showing an unengaged attachment mechanism of one of the band members in FIG. 1A;

FIG. 2B is a perspective view showing the attachment mechanism of FIG. 2A in an engaged configuration;

FIG. 2C is a perspective view showing an alternative configuration of the attachment mechanism in. FIG. 2A;

FIG. 2D is a perspective view showing the attachment mechanism in FIG. 2C in an engaged configuration;

FIG. 2E is a perspective view showing an alternative configuration of the attachment mechanism in FIG. 2A;

FIG. 2F is a perspective view showing the attachment mechanism in FIG. 2E in an engaged configuration;

FIG. 2G is a perspective view showing an alternative configuration of the attachment mechanism in FIG. 2A;

FIG. 2H is a perspective view showing the attachment mechanism in FIG. 2G in an engaged configuration;

DETAILED DESCRIPTION

The present invention relates generally to a preformed gastric band, and more particularly to a preformed gastric band for preventing or mitigating dilation of a gastric pouch following a gastric bypass procedure. FIGS. 1A-D illustrate one aspect of the present invention comprising a preformed gastric band 10 for preventing or mitigating dilation of a gastric pouch 12 (FIG. 4) following a gastric bypass procedure. Unlike gastric bands of the prior art, which must be created in the operating room (OR) during a banded bypass procedure, the present invention reduces the time needed for surgery by providing a preformed gastric band 10 (FIG. 1A) that can be easily sized and quickly placed. Additionally, the preformed gastric band 10 of the present invention can be readily removed should the gastric band need to be replaced, which eliminates the need for additional invasive surgery.

I. Preformed Gastric Band

One aspect of the present invention provides a preformed gastric band 10 comprising a flexible substrate 14 and a plurality of band members 16 securely connected thereto. The gastric band 10 is formed prior to a banded bypass surgery. A banded bypass surgery is one in which a previously-formed gastric pouch 12 (FIG. 4) is "banded" to prevent or mitigate subsequent dilation of the gastric pouch. The gastric band 10 (FIG. 1A) can move between an unfolded configuration (shown in FIG. 1A) and a folded configuration (FIG. 1D). As discussed above, formation of the gastric band 10 prior to surgery is advantageous because it saves critical time by eliminating the need for a surgeon to create each band de novo in the OR.

(a) Flexible Substrate 14

Figure 4:
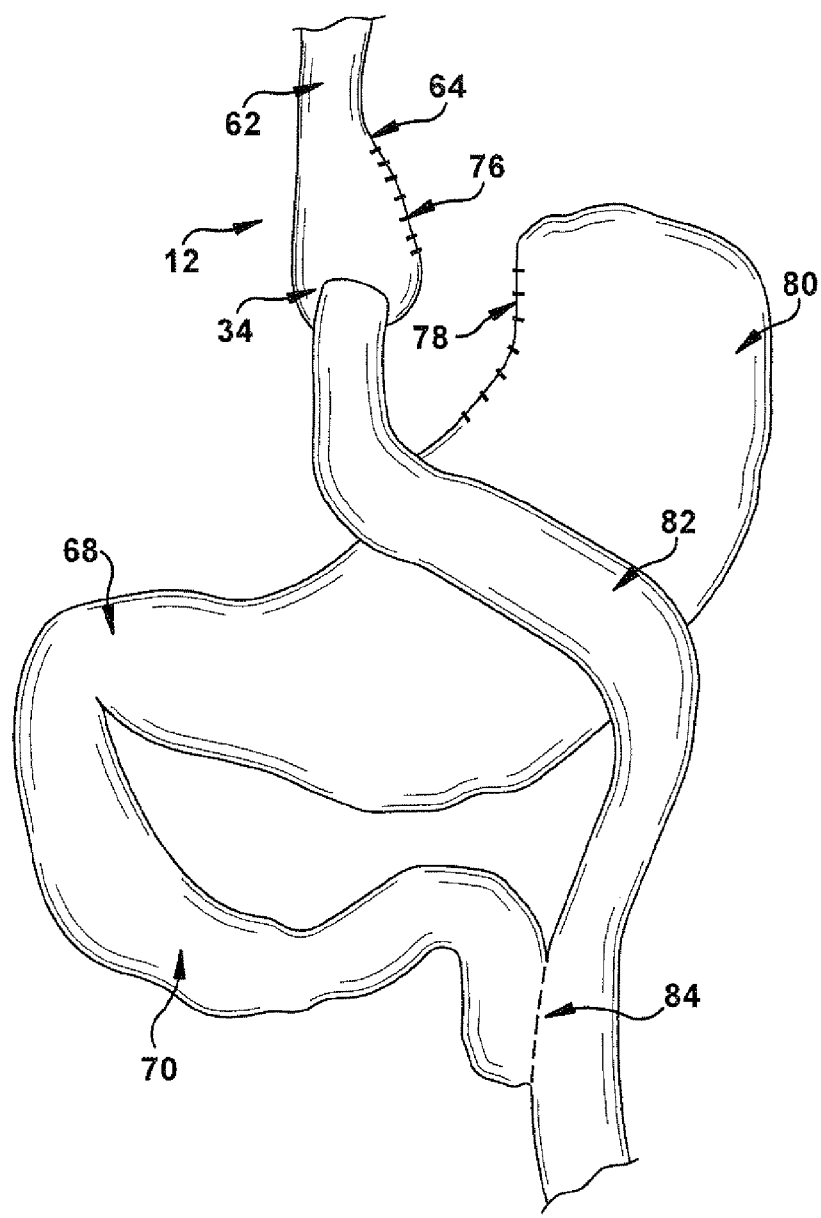
FIG. 4 is a schematic illustration showing GI anatomy status-post Roux-en-Y bypass.

In another aspect of the present invention, the preformed gastric band 10 comprises a flexible substrate 14 for attachment to a gastric pouch 12 (FIG. 4). The flexible substrate 14 (FIG. 1A) serves as a platform for attachment of the plurality of band members 16. Additionally, the substrate 14 is sufficiently flexible or pliable to allow the substrate to be wrapped around substantially the entire gastric pouch 12 (FIG. 4). Although the substrate 14 is shown in FIGS. 1A-D as having a generally rectangular shape, it will be appreciated that the substrate can have any shape that permits the substrate to be wrapped around substantially the entire the gastric pouch 12 (FIG. 4).

Figure 1A:
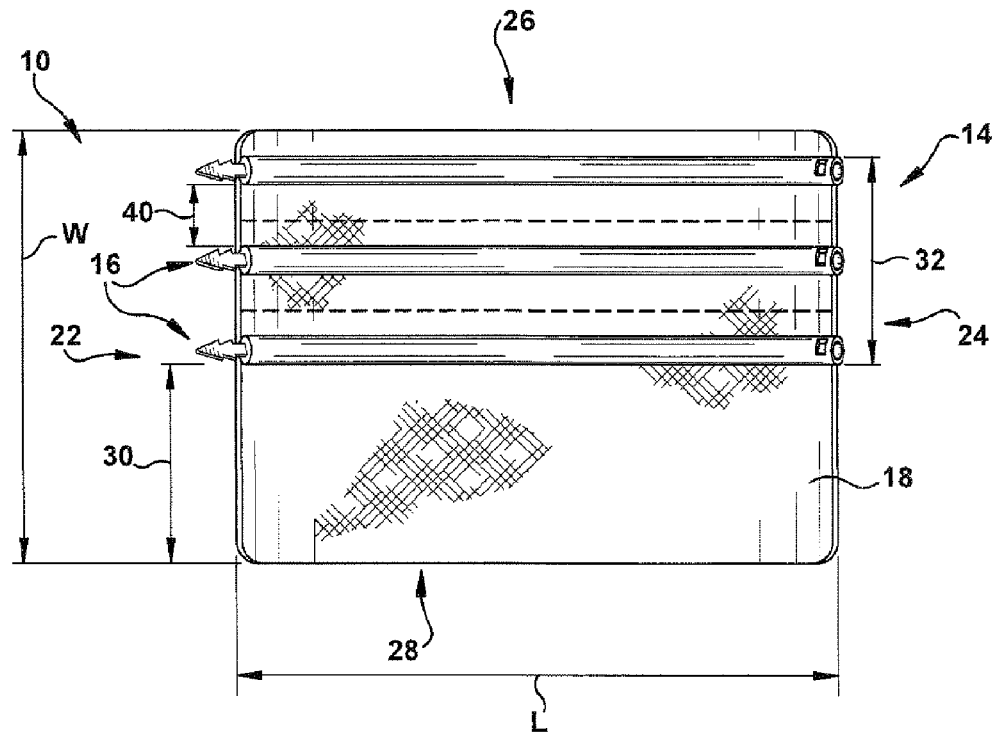
FIG. 1A is a perspective view of a preformed gastric band (unfolded configuration) comprising a flexible substrate and a plurality of flexible band members securely connected thereto and being constructed in accordance with one aspect of the present invention.
Figure 1B:
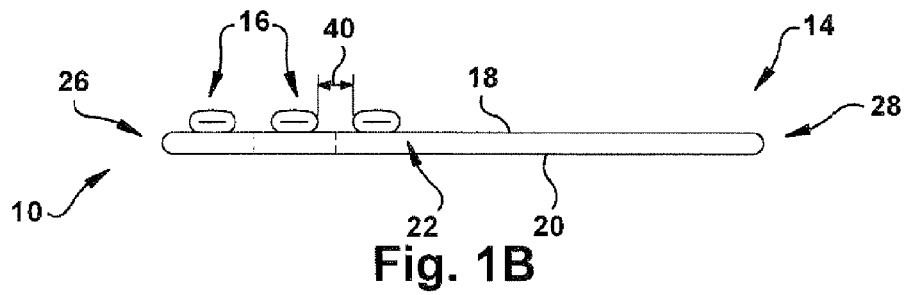
FIG. 1B is a side view of the gastric band in FIG. 1A taken along a minor side portion of the gastric band.

As shown in FIGS. 1A-B, the substrate 14 comprises oppositely disposed first and second major surfaces 18 and 20 that are defined by first and second minor side portions 22 and 24 and first and second major side portions 26 and 28. The first and second minor side portions 22 and 24 generally define a width W of the substrate 14, and the first and second major side portions 26 and 28 generally define a length L of the substrate. Although the actual dimensions of the substrate 14 will vary depending upon the anatomy of a particular subject, the width W of the substrate can be about 2 cm to about 8 cm, and the length L of the substrate can be about 4 cm to about 10 cm. In one example of the present invention, the width W of the substrate 14 can be about 4 cm, and the length L can be about 6.5 cm.

The first major surface 18 of the substrate 14 includes a lower collar section 30 and an upper band section 32. The upper band section 32 is adapted to receive and secure the plurality of band members 16 thereto. The lower collar section 30 is configured to buffer the upper band section 32 from an anastomosis 34 (FIG. 4) that is formed as part of the gastric bypass procedure. As shown in FIG. 1A, the absence or lack of band members 16 about the first major surface 18 defines the lower collar section 30 of the substrate 14. The dimensions of the upper band section 32 and the lower collar section 30 can be varied as needed and are not necessarily equal to one another. As discussed in more detail below, the upper band section 32 and/or the lower collar section 30 can be sized (e.g., trimmed) prior to implantation of the gastric band 10 to accommodate the anatomy of the gastric pouch 12 (FIG. 4).

All or only a portion of the substrate 14 can additionally include at least one hair-like projection (not shown) for preventing the gastric band 10 from distal migration following implantation. The hair-like projections can be disposed about the second major surface 20 of the substrate 14 and be formed of the same or different material as the substrate. The hair-like projections can be separately attached to the second major surface 20 or formed as an integral part thereof. When the gastric band 10 is implanted in a subject, the hair-like projections can contact the gastric pouch 12 (FIG. 4) and/or the anastomosis 34 to prevent the substrate 14 from migrating distally towards the distal anastomosis 84.

The substrate 14 (FIG. 1A) additionally or optionally includes at least one perforation (indicated by dashed line) that extends between the first and second minor side portions 22 and 24. As described in more detail below, the perforation allows one or more pre-determined sections of the substrate 14 to be easily removed (e.g., by trimming or tactile force) prior to implantation of the gastric band 10. For example, the width W of the substrate 14 can be quickly adjusted in the OR upon determining the measured dimensions of the gastric pouch 12 (FIG. 4). The presence of one or more perforations in the substrate 14 (FIG. 1A) can thus reduce the time and effort needed to customize the gastric band 10 in the OR.

At least a portion of the substrate 14 is made of a bioabsorbable and/or non-bioabsorbable material. Bioabsorbable materials may be at least partially absorbable by the body and include, for example, one or a combination of bioabsorbable polymers or copolymers. Bioabsorbable polymers can include polymers whose degradation by-products can be bio-assimilated or excreted via natural pathways in a subject's body. It will be appreciated that the absorption or degradation rate of the material can be logarithmic such that substantially all of the material is degraded or absorbed over a desired period of time (e.g., one year). Examples of bioabsorbable polymers can include polyglycolic acid (PGA), polylactic acid (PLA), polycaprolactone or polyhydroxyalkanoate, as well as tissue-based materials, such as pericardial tissue, collagen, or other biological materials or tissues obtained from a subject who is to receive the gastric band 10, from another person, or from a tissue engineering process. Examples of non-bioabsorbable materials can include non-absorbable polymers, such as polypropylene, polyethylene, terephthalate, polytetrafluoroethylene (PTFE), expanded PTFE (ePTFE), polyaryletherketone, nylon, fluorinated ethylene propylene, polybutester, silicone, and/or copolymers thereof.

In one example of the present invention, at least a portion of the substrate 14 can be made of a bioabsorbable and/or non-bioabsorbable mesh. The bioabsorbable and/or non-bioabsorbable mesh can comprise an open material, fabric, or structure having a plurality of spaced apart pores or openings. For instance, the substrate 14 can be made of a non-absorbable ePTFE mesh or, alternatively, a bioabsorbable synthetic mesh made of polyglycolic acid:trimethylene carbonate fibers (e.g., GORE BIO-A, which is commercially available from W.L. Gore & Associates, Flagstaff, Ariz.). The mesh is at least partially porous to promote tissue in-growth and/or bioabsorption (i.e., when the mesh is comprised of a bioabsorbable material). The mesh can have the same or varying pore size, depending upon the intended construction of the gastric band 10.

Figure 1C:
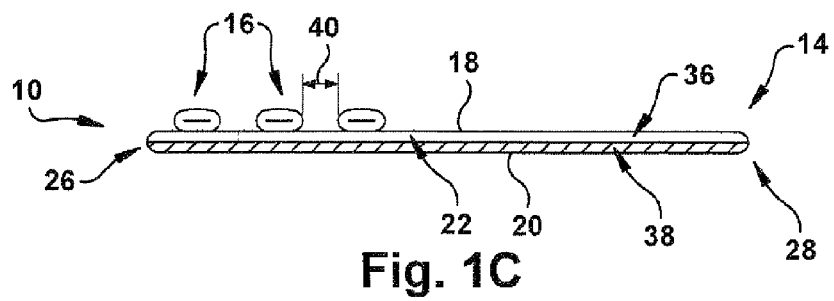
FIG. 1C is a side view showing an alternative configuration of the gastric band in FIG. 1B.
Figure 1D:
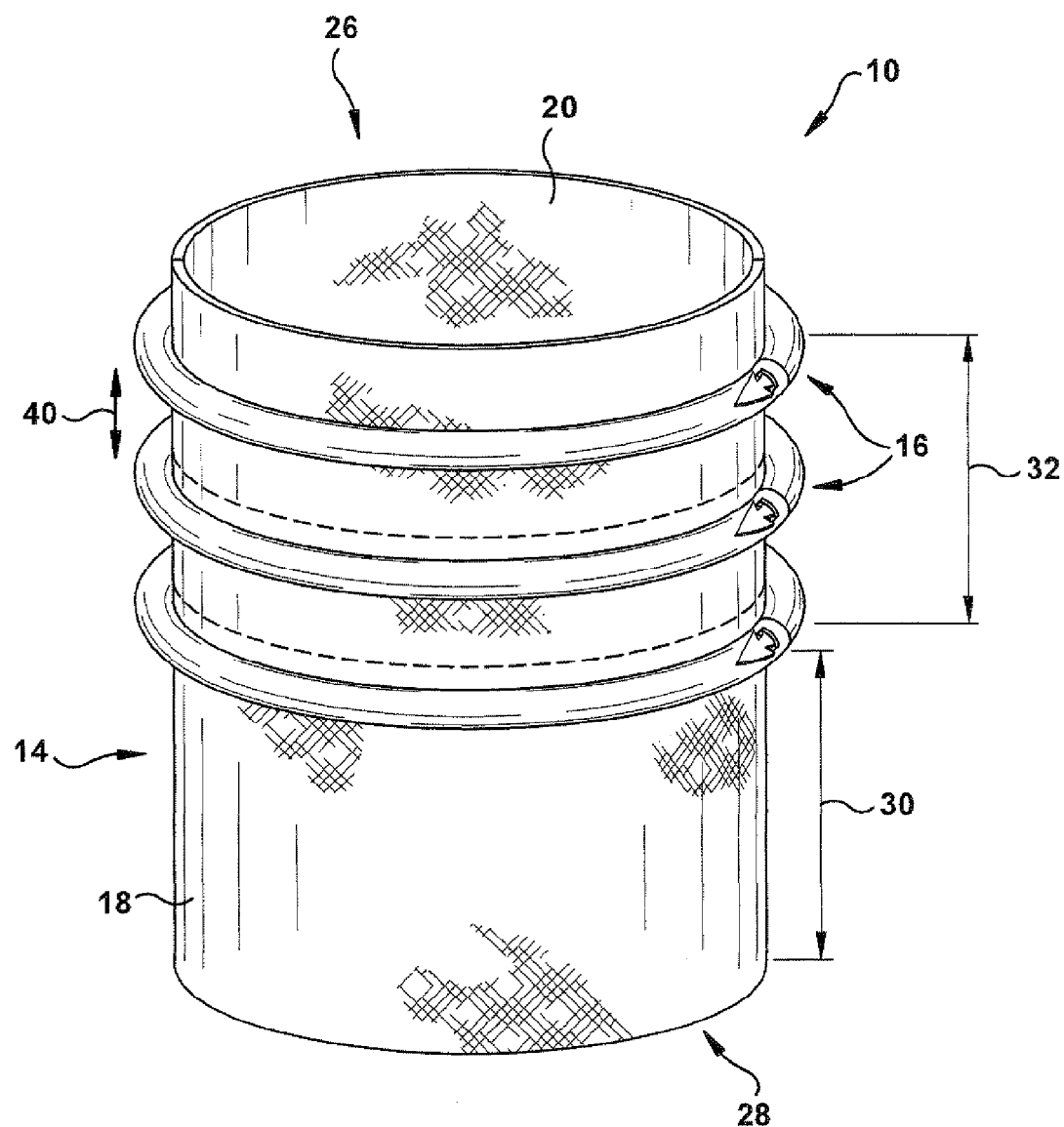
FIG. 1D is a perspective view showing the gastric band in FIG. 1A in a folded configuration.

The substrate 14 can have a monolayer (FIGS. 1A-B) or multilayer construction (FIG. 1C). As shown in FIG. 1C, for example, the substrate 14 can comprise first and second adjacent layers 36 and 38 that are made of the same or different materials. For instance, the first layer 36 can be comprised of a non-bioabsorbable material, and the second layer 38 can be comprised of a bioabsorbable material. Alternatively, the material comprising the first layer 36 can have a slower absorption rate than the second layer 38. Additionally, where a mesh material is used to form the first and second layers 36 and 38, the first layer may have a higher pore density than the second layer or, alternatively, the first layer may have a smaller pore size than the second layer.

(b) Flexible Band Members 16

In another aspect of the present invention, a plurality of flexible band members 16 is securely connected to the first major surface 18 of the substrate 14. The band members 16 can be securely disposed on or mounted to the first major surface 18 of the substrate 14 using one or a combination of attachment devices (e.g., stitches, clips, adhesive, etc) (not shown). Alternatively, one or more of the band members 16 can be disposed within all or only a portion of the substrate 14. The band members 16 are sufficiently flexible or elastic to allow a food bolus to pass through the gastric pouch 12 (FIG. 4), yet rigid enough to prevent the gastric pouch from over dilating and becoming unstable over time.

Although only three band members 16 are shown in FIGS. 1A-D, it will be appreciated that any number of band members can be connected to the substrate 14. As described in more detail below, the band members 16 provide a sufficient degree of tension about the gastric pouch 12 (FIG. 4) once implanted. To ensure that substantially uniform, long-term tension is applied, it may be desirable to include two or more band members 16 (FIG. 1A) as part of the gastric band 10 to provide redundant support mechanisms in the event that one of the band members breaks or otherwise becomes dysfunctional.

Each of the band members 16 extends between the first and second minor side portions 22 and 24 of the substrate 14, and is made of a flexible, biologically inert material, such as a silastic material (e.g., silicone) or nylon (e.g., 2 mm nylon rings). Additionally, each of the band members 16 includes a length that is substantially equal to the length L of the substrate 14. Each of the band members 16 is spaced apart from one another by a spacing region 40. The spacing region 40 can have a width of about 2 mm to about 7 mm. In one example of the present invention, the spacing region 40 can have a width of about 5 mm. Each spacing region 40 can additionally or optionally include at least one perforation. As discussed above, the perforation allows a pre-determined section or sections of the substrate 14 to be easily removed (e.g., by trimming or tactile force) prior to implantation of the gastric band 10.

Referring to FIGS. 2A-H, each of the band members 16 includes first and second ends 42 and 44 that comprise an attachment mechanism for connecting the first and second ends. Generally, the attachment mechanism can comprise any one or combination of male/female, friction fit, press fit, or magnet connections that securely mate the first and second ends 42 and 44 and thereby form each of the band members 16 into a ring-like configuration. Although not shown in the Figures, it will be appreciated that each of the band members 16 can include a point of failure that is substantially opposite the attachment mechanism such that there would not be two discrete ends free to perforate a nearby structure should a band member need to be propped open. A variety of attachment mechanisms are shown in FIGS. 2A-H, all of which are intended to be illustrative only and not limiting of the present invention.

One example of the attachment mechanism is shown in FIGS. 1A-2B. The attachment mechanism has a "zip-tie" configuration and includes a multi-toothed, plano-flexible barb 46 (FIG. 2A) disposed at the first end 42 of the band member 16. The barb 46 can be made of a rigid or semi-rigid material (e.g., a metal, metal alloy, or plastic), and can be fluidly formed from the band member 16 itself or separately attached thereto (e.g., embedded therein). The second end 44 of the band member 16 can include an aperture 48 for receiving the barb. As shown in FIG. 2B, the barb 46 can be mated with the aperture 48 to form a ring-like structure. The diameter of the resultant ring-like structure can be adjusted (e.g., reduced) by advancing the barb 46 through aperture 48 so that the teeth 50 of the barb are progressively "locked" into place about the aperture.

Another example of the attachment mechanism is shown in FIGS. 2C-D. Similar to the attachment mechanism in FIGS. 2A-B, the first end 42 of the band member 16 includes a multi-toothed, piano-flexible barb 46. The second end 44 of the band member 16 includes a cavity 52 having a shape that is adapted to receive all or only a portion of the barb 46. As shown in FIG. 2D, the ring-like structure formed by the attachment mechanism can be adjusted (e.g., reduced) to a desired diameter by inserting the barb 46 into the cavity 52 and then progressively advancing the barb until the teeth 50 are "locked" in place within the cavity.

Another example of the attachment mechanism is shown in FIGS. 2E-F. The attachment mechanism comprises first and second Velcro sections 54 and 56 (FIG. 2E) that are securely mounted to the first and second ends 42 and 44 (respectively) of the band member 16. The use of Velcro sections 54 and 56 is advantageous as most users are familiar with attaching it, it allows for multiple adjustments, and its relative ease of fabrication. The size and location of the first and second Velcro sections 54 and 56 about the band member 16 are configured so that the first and second ends 42 and 44 become securely fastened to one another upon contacting the first and second Velcro sections with one another (FIG. 2F). The first and second Velcro sections 54 and 56 can be made of one or more biocompatible materials, such as Nylon.

Another example of the attachment mechanism is shown in FIGS. 2G-F. Generally, the attachment mechanism can have a configuration similar to a common light fixture pull chain. For example, the first end 42 of the band member 16 can include a receptacle member 58, and the second end 44 of the band member can include a plurality of spaced apart connection members 60. The receptacle member 58 and the connection members 60 can be formed from the same or different material as the band member 16. Additionally, the receptacle member 58 and the connection members 60 can be separately connected to the band member 16 itself or, alternatively, formed as a fluid part (e.g., molded) of the band member. As shown in FIG. 2H, the receptacle member 58 can be mated with one of the connecting members 60 to form a ring-like structure. The diameter of ring-like structure can be adjusted as needed by mating the receptacle member 58 to a different one of the connecting members 60.

II. Method of Use

Gastric bypass procedures generally seek to promote weight loss through at least one of two mechanisms: (1) creating a restrictive effect (e.g., by reducing the effective volume of the stomach); and/or (2) creating a malabsorptive effect (e.g., by creating an intestinal bypass). The present invention is used to augment a variety of surgical gastric bypass procedures used to induce weight loss in morbidly obese patients. For example, the present invention can find use in the Roux-en-Y gastric bypass (RYGB), sleeve gastrectomy, sleeve gastrectomy with duodenal switch or biliopancreatic diversion, vertical banded gastroplasty (VBG), VBG with bypass, Magenstrasse and Mill procedure, adjustable gastric banding, and revisional operations.

Figure 3:
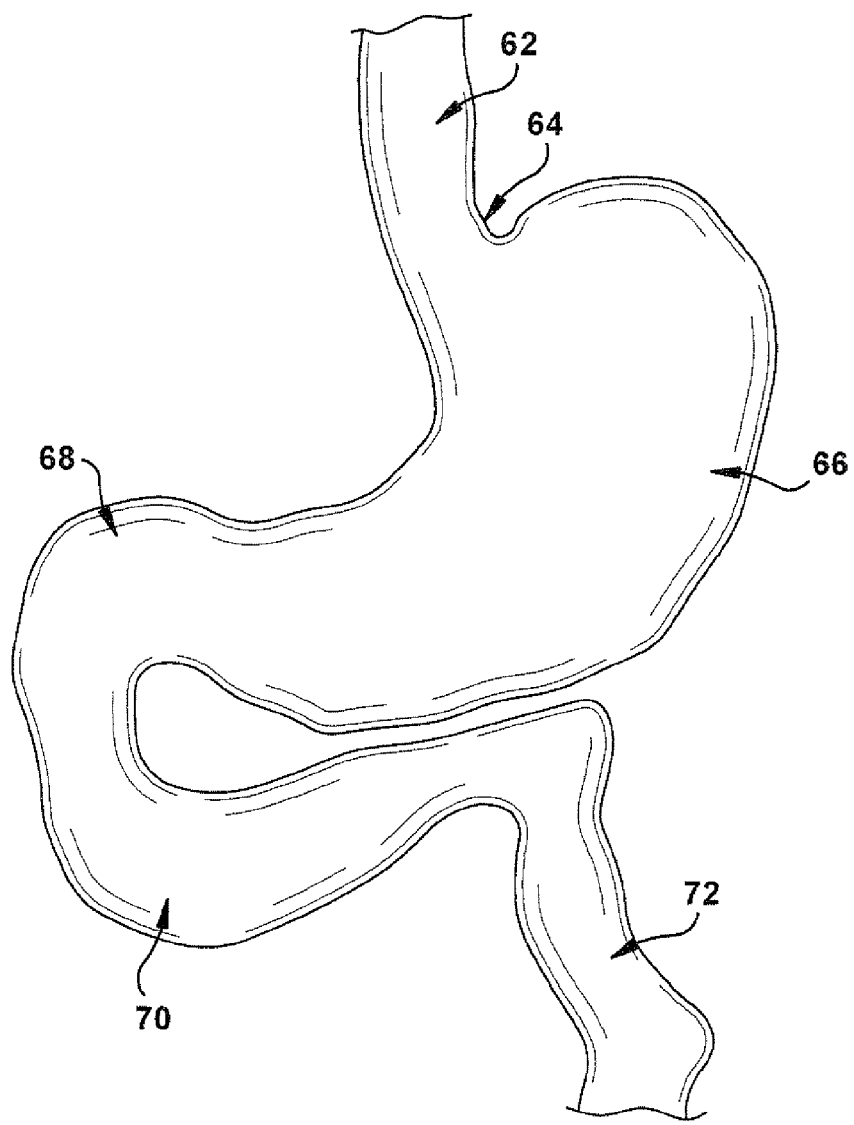
FIG. 3 is a schematic illustration showing normal gastrointestinal (GI) anatomy.

The normal native stomach anatomy is shown in FIG. 3, illustrating the esophagus 62, gastro-esophageal junction 64, stomach 66, pylorus 68, duodenum 70, and jejunum 72. Gastric bypass procedures such that those described above, with the exception of gastric banding, permanently alter the gastrointestinal anatomy of a subject.

In one aspect of the present invention, a method is provided for restricting expansion of a gastric pouch 12 in a subject. As discussed above, the gastric pouch 12 can be formed during a gastric bypass procedure. As is common to several of the gastric bypass procedures noted above, the gastric pouch 12 can also include an anastomosis 34 (e.g., with a bowel section 74). In one example of the present invention, the gastric pouch 12 can be formed during laparoscopic RYGB. FIG. 4 illustrates anatomy status-post RYGB, which includes the esophagus 62, gastro-esophageal junction 64, gastric pouch 12 (also sometimes referred to as the neo-stomach), gastric pouch staple or suture lines 76, bypassed stomach staple or suture lines 78, bypassed stomach 80 and pylorus 68, duodenum 70, proximal anastomosis 34, Roux intestinal limb 82, and distal intestinal anastomosis 84.

Figure 5:
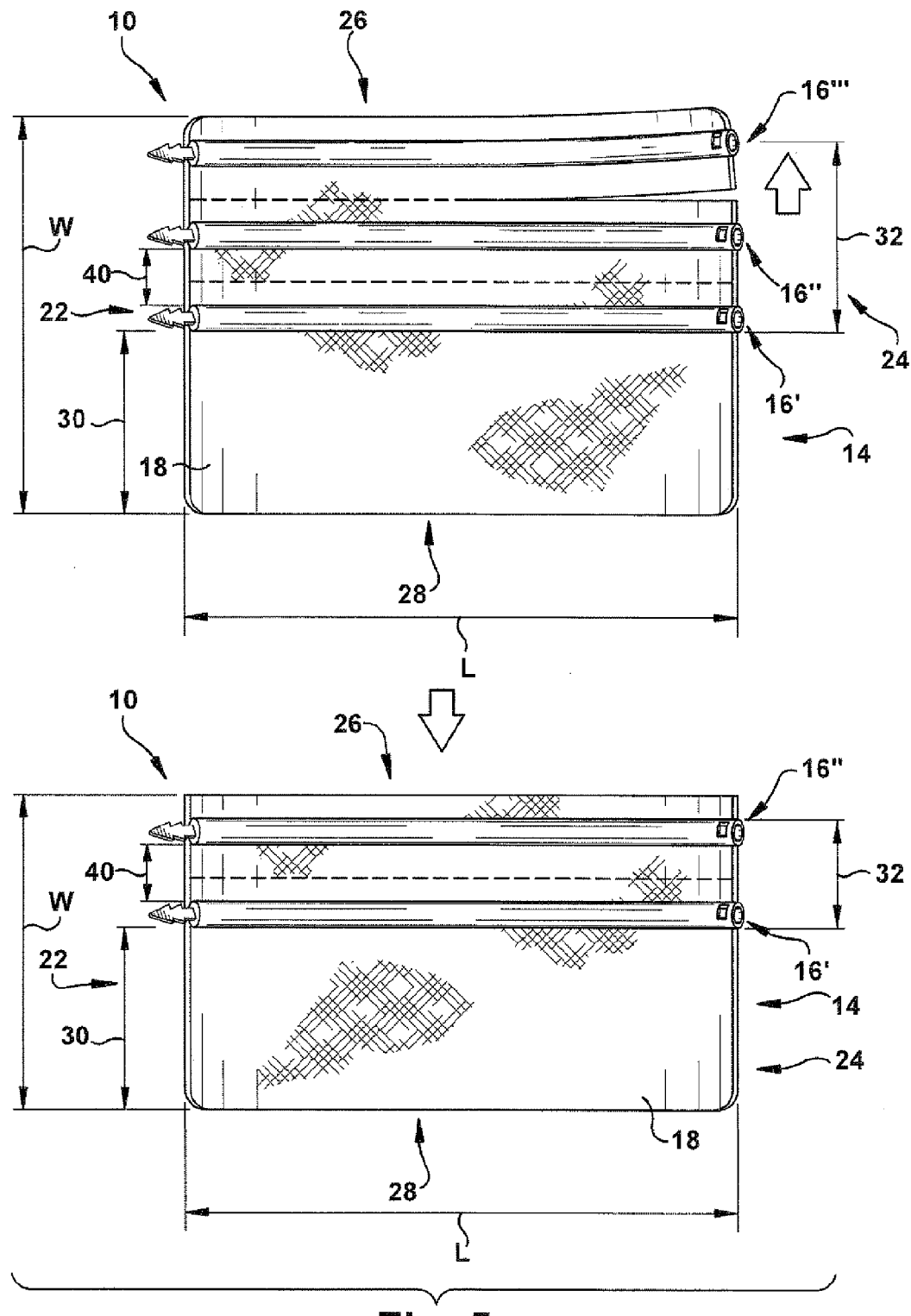
FIG. 5 is a schematic illustration showing the gastric band of FIG. 1A being sized to the dimensions of a gastric pouch.

One step of the method includes providing a gastric band 10 (FIG. 5). As described above, the gastric band 10 comprises a flexible substrate 14 having a plurality of flexible band members 16 connected thereto. In one example of the present invention, the gastric band 10 can have a configuration similar to the one in FIGS. 1A-B. For instance, the gastric band 10 can include first, second, and third band members 16', 16", and 16' that are each securely disposed on the first major surface 18 of a biodegradable mesh substrate 14. The gastric band 10 can have a length L of about 6.5 cm and width W of about 3-4 cm. Additionally, the width of each of the spacing regions 40 can be about 5 mm.

After providing the gastric band 10, the gastric pouch 12 is visualized to determine the dimensions of the gastric pouch. The dimensions of the gastric pouch 12 can be determined upon gross inspection, e.g., immediately following an open or laparoscopic procedure. Alternatively, the dimensions of the gastric pouch 12 can be determined using one or a combination of known imaging modalities, such as ultrasound, magnetic resonance imaging, nuclear magnetic resonance.

Depending upon the measured dimensions of the gastric pouch 12, the gastric band 10 is optionally sized so that the second major surface 20 of the substrate 14 can be wrapped around the substantial entirety of the gastric pouch. As discussed above, the gastric band 10 can be optimally sized by trimming a portion of the substrate 14 and/or removing one or more of the band members 16. Where the width W of the substrate 14 needs to be reduced, for example, the third band member 16''' can be removed by applying a tactile force (indicated by the darkened arrow in FIG. 5) to the first major side portion 26 of the substrate 14, thereby tearing the substrate along the perforation.

Figure 6:
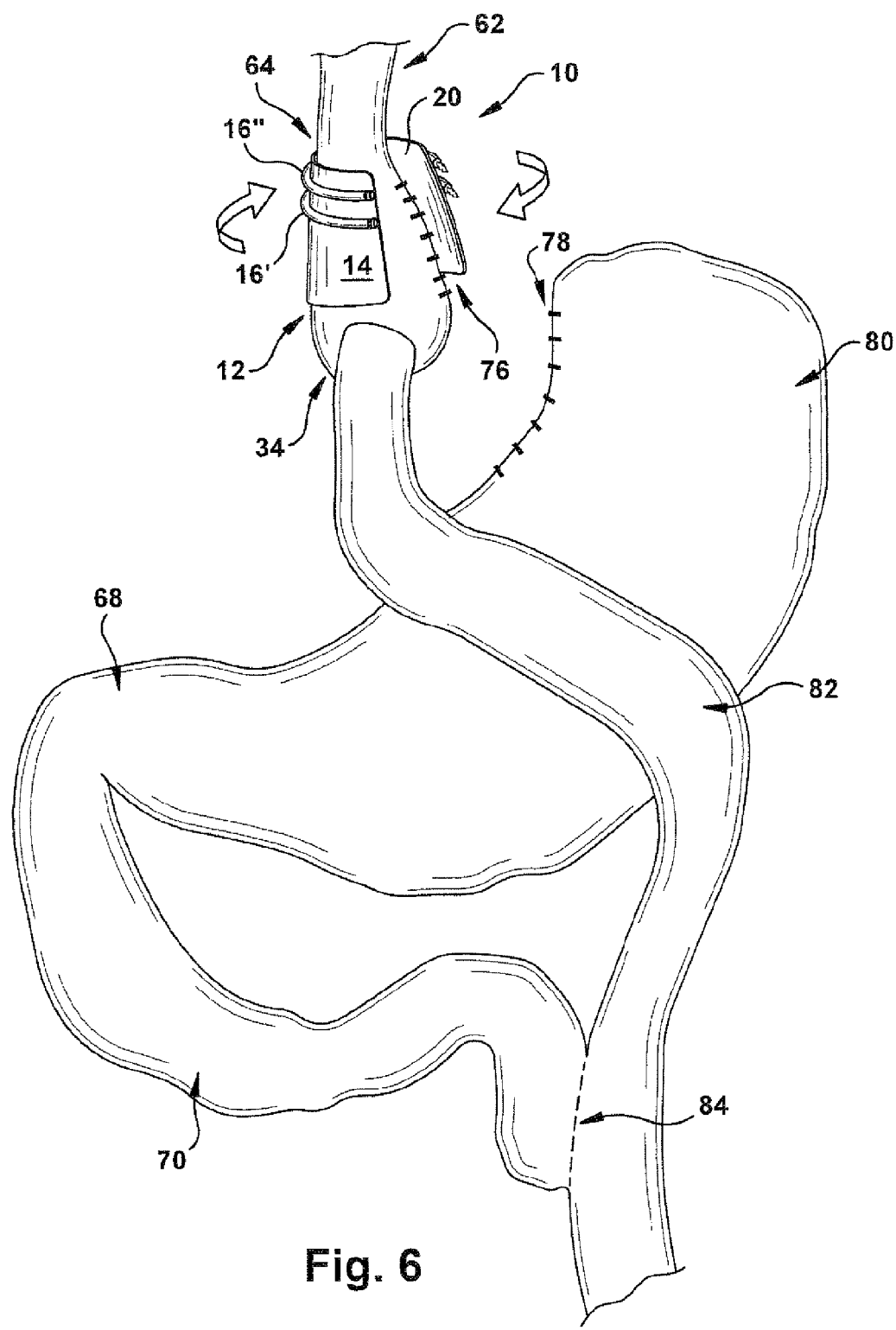
FIG. 6 is a schematic illustration showing the gastric band of FIG. 5 being wrapped around the gastric pouch.
Figure 7:
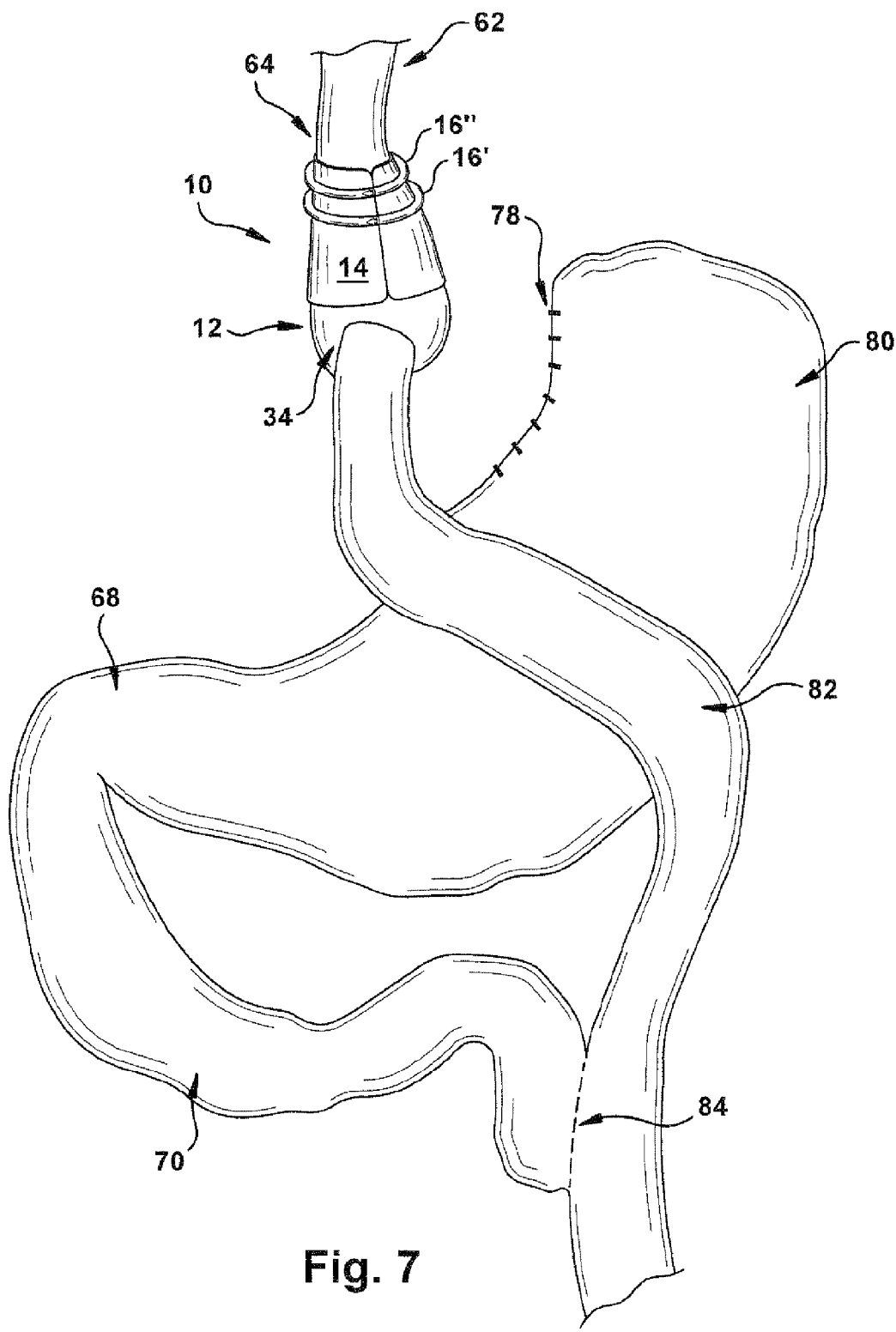
FIG. 7 is a schematic illustration showing the gastric band in FIG. 6 secured to the gastric pouch.

Next, the second major surface 20 of the substrate 14 is contacted with the gastric pouch 12. During a laparoscopic procedure, for example, the gastric band 10 can be placed via a first port (not shown) and then manipulated as needed through a second port (not shown). As shown in FIG. 6, the second major surface 20 is wrapped around the gastric pouch 12 so that the lower collar section 30 of the substrate 14 is located proximal to the anastomosis 34. Placement of the lower collar section 30 as shown in FIG. 6 prevents unwanted contact between the band members 16' and 16" and the anastomosis 34 following implantation of the gastric band 10, may cause rubbing or tearing at or near the anastomosis. Next, the substrate 14 is progressively wrapped around the gastric pouch 12 until the first and second ends 42 and 44 of each of the first and second band members 16' and 16" is adjacent one another. The substrate 14 is then secured in place (e.g., by stitches).

Once the substrate 14 has been secured in place and the first and second ends 42 and 44 of each of the first and second band members 16' and 16" are adjacent one another, the attachment mechanism of each of the band members is manipulated to secure the gastric band 10 about the gastric pouch 12. Where each of the attachment mechanisms comprise a barb 46 and aperture 48 configuration, the barb can be mated with the aperture so that each of the first and second band members 16' and 16" obtains a ring-like configuration (as described above). If needed, the diameter of each of the ring-like first and second band members 16' and 16" can be adjusted (e.g., reduced) by advancing the barb(s) 46 through aperture(s) 48 so that the teeth 50 of the individual barb(s) is/are progressively "locked" into place about the respective aperture(s).

The tension of each of the first and second ring members is sufficiently set so that a food bolus can pass into and out of the gastric pouch without excessively dilating the gastric pouch. The present invention keeps the newly created gastric pouch stable over time, which reduces or eliminates the likelihood of weight regain in the subject.

It will be appreciated that all or a portion of the gastric band can be removed or replaced, if needed, without the need for an additional operation. For example, an endoscopy can be performed to partly or entirely remove the gastric band from the subject without having to perform another open or laparoscopic procedure.

From the above description of the invention, those skilled in the art will perceive improvements, changes and modifications. Such improvements, changes, and modifications are within the skill of one in the art and are intended to be covered by the appended claims.

Having described the invention, the following is claimed:

1. A preformed gastric band for restricting expansion of a gastric pouch in a subject, the gastric pouch being formed by a bariatric procedure and including an anastomosis, said preformed gastric band comprising:

a flexible substrate comprising oppositely disposed first and second major surfaces defined by first and second minor side portions and first and second major side portions, said first major surface including a lower collar section and an upper band section, the upper band section being disposed between the lower collar section and the first major side portion, the lower collar section extending from the upper band section to the second major side portion;

a plurality of flexible band members securely connected to only the upper band section of the first major surface to prevent contact between said band members and the anastomosis, each of said band members extending between said first and second minor side portions of said substrate, each of said band members including first and second ends that comprise an attachment mechanism for connecting said first and second ends, each of said band members being separated from one another by a spacing region, all of the band members being absent from the lower collar section; and a plurality of perforations provided on the spacing region, said plurality of perforations arranged in a line extending between said first and second minor portions and only substantially parallel to said plurality of flexible band members, said plurality of perforations being configured to allow said flexible substrate to tear along said line.

2. The preformed gastric band of claim 1, wherein at least a portion of said substrate is formed from a mesh material.

3. The preformed gastric band of claim 1, wherein at least a portion of said substrate comprises a bioabsorbable material.

4. The preformed gastric band of claim 1, wherein at least a portion of said substrate comprises a non-bioabsorbable material.

5. The preformed gastric band of claim 1, wherein said substrate further comprises:
an upper non-bioabsorbable layer; and
a lower bioabsorbable layer.

6. The preformed gastric band of claim 1, wherein at least one of said plurality of band members is formed from a silastic material.

7. The preformed gastric band of claim 1, wherein at least one of said plurality of band members includes a coil member.

8. The preformed gastric band of claim 1, wherein only a single line of perforations is provided between adjacent band members of said plurality of band members.

9. A method for restricting expansion of a gastric pouch in a subject, the gastric pouch being formed by a bariatric procedure and including an anastomosis, said method comprising the steps of:
providing a gastric band comprising a flexible substrate, a plurality of band members disposed thereon, and a plurality of perforations provided on the flexible substrate, the flexible substrate comprising oppositely disposed first and second major surfaces defined by first and second minor side portions and first and second major side portions, the first major surface including a lower collar section and an upper band section, the upper band section being disposed between the lower collar section and the first major side portion, the lower collar section extending from the upper band section to the second major side portion, the plurality of band members being securely disposed on only the upper band section of the first major surface to prevent contact between the band members and the anastomosis, each of the band members extending between the first and second minor side portions of the substrate, each of the band members including first and second ends that comprise an attachment mechanism for connecting the first and second ends, each of the band members being separated from one another by a spacing region, all of the band members being absent from the lower collar section, the plurality of perforations arranged in a line extending between the first and second minor portions and only substantially parallel to the plurality of band members, the plurality of perforations being configured to allow the flexible substrate to tear along the line;

determining the dimensions of the gastric pouch;

optionally sizing the gastric band based on the determined dimensions of the gastric pouch; and securing the gastric band to the gastric pouch;

wherein the gastric band prevents or mitigates dilation of the gastric pouch.

10. The method of claim 9, wherein said step of sizing the gastric band includes trimming at least a portion of the substrate.

11. The method of claim 9, wherein said step of sizing the gastric band includes removing one of the band members.

12. The method of claim 9, wherein said step of securing the gastric band further comprises the steps of:
wrapping the substrate around the gastric pouch so that the first and second ends of each of the plurality of band members are proximate one another;
engaging the attachment mechanism of each of the plurality of band members so that each of the plurality of band members obtains a ring-like configuration about the gastric pouch; and
optionally manipulating the attachment mechanism of the plurality of band members to adjust a diameter of each of the plurality of band members.

13. The method of claim 9 being performed via an open surgical procedure.

14. The method of claim 9 being performed via a laparoscopic procedure.

15. The method of claim 9 further comprising the step of endoscopically removing at least a portion of the gastric band from the subject.

16. A preformed gastric band comprising:
a flexible substrate comprising oppositely disposed first and second major surfaces defined by first and second minor side portions and first and second major side portions, the first major surface including a lower collar section and an upper band section, the upper band section being disposed between the lower collar section and the first major side portion, the lower collar section extending from the upper band section to the second major side portion;
a plurality of flexible band members securely connected to the upper band section and extending between the first and second minor side portions of the substrate, each of the band members including first and second ends that comprise an attachment mechanism for connecting the first and second ends, each of the band members being separated from one another by a spacing region, all of the band members being located within the upper band section and being absent from below the upper band section; and
perforations provided on said spacing region that extend between said first and second minor side portions, said perforations being located only in the upper band section and being configured to allow one or more pre-determined sections of the substrate to be easily removed.

* * * * *